(12) United States Patent
Whitcher et al.

(10) Patent No.: US 6,273,901 B1
(45) Date of Patent: Aug. 14, 2001

(54) THROMBOSIS FILTER HAVING A SURFACE TREATMENT

(75) Inventors: Forrest D. Whitcher, Allston, MA (US); Alan Kaganov, Portola Valley, CA (US); Sally C. Thornton, Marlborough, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/371,305

(22) Filed: Aug. 10, 1999

(51) Int. Cl.[7] .................................. A61M 29/00
(52) U.S. Cl. ............................................ 606/200
(58) Field of Search ...................... 606/200, 191

(56) References Cited

U.S. PATENT DOCUMENTS

| | | | |
|---|---|---|---|
| 3,334,629 | 8/1967 | Cohn | 128/325 |
| 3,467,102 | 9/1969 | Fogarty et al. | 128/348 |
| 3,540,431 | 11/1970 | Mobin-Uddin | 128/1 |
| 3,868,956 | 3/1975 | Alfidi et al. | 128/345 |
| 3,952,747 | 4/1976 | Kimmell, Jr. | 128/303 |
| 4,391,797 | 7/1983 | Folkman et al. | 424/19 |
| 4,425,908 | 1/1984 | Simon | 128/1 |

(List continued on next page.)

FOREIGN PATENT DOCUMENTS

| | | |
|---|---|---|
| 0 117 940 A2 | 9/1984 | (EP) . |
| 0 270 432 B1 | 6/1988 | (EP) . |
| 0 293 605 A1 | 12/1988 | (EP) . |
| 0 350 043 B1 | 1/1990 | (EP) . |
| 0 430 848 A1 | 6/1991 | (EP) . |
| 0 472 334 A1 | 2/1992 | (EP) . |
| 2 573 646 | 11/1984 | (FR) . |
| 2 570 288 | 3/1986 | (FR) . |
| 2 580 504 | 10/1986 | (FR) . |
| WO 92/03097 | 3/1992 | (WO) . |
| WO 93/12723 | 7/1993 | (WO) . |
| WO 97/33552 A1 | 9/1997 | (WO) . |

OTHER PUBLICATIONS

J.J. Alexander, B.L. Gewertz, Chien–Tai Lu and C.K. Zarins, "New Criteria for Placement of a Prophylactic Vena Cava Filter," pp. 405–409, Nov. 1986, *Surgery Gynecology & Obstetrics*, 163.

M.H. Awh, F.C. Taylor and Chien–Tai Lu, "Spontaneous Fracture of a Vena–Tech Inferior Vena Caval Filter", pp. 177–178, 1991, *AJR*, 157.

Castaneda–Zuniga et al., "Seminars in Interventional Radiology," pp. 175–241, 1986, *Thieme Medical Publishers, Inc.*, 3.

A Cragg, G. Lund, E. Salomonowitz, J. Rysavy, F. Castaneda, W. Castaneda–Zuniga, K. Amplatz, "A New Percutaneous Vena Cava Filter," pp. 601–604, 1983, *AJR*, 141.

(List continued on next page.)

*Primary Examiner*—Jeffrey A. Smith
(74) *Attorney, Agent, or Firm*—Crompton, Seager & Tufte, LLC

(57) ABSTRACT

A thrombosis filter configured for placement within a blood vessel lumen. The thrombosis filter of the present invention includes a body element, a plurality of struts, and a surface treatment. The surface treatment, comprised in part of an anti-proliferative or anti-angiogenic drug, is applied to portions of the thrombosis filter in order to regulate neointimal growth around the thrombosis filter and its anchor elements. The thrombosis filter may further contain a first and a second surface treatment layer. The first surface treatment layer possesses endothelial cell growth enhancing properties, while the second surface treatment layer includes the anti-proliferative or anti-angiogenic drug. The surface treatment may alternatively be applied to a substrate, which in turn is applied to the filter.

17 Claims, 4 Drawing Sheets

U.S. PATENT DOCUMENTS

| | | | |
|---|---|---|---|
| 4,430,081 | 2/1984 | Timmermans | 604/256 |
| 4,459,317 | 7/1984 | Lambert | 427/2 |
| 4,487,808 | 12/1984 | Lambert | 428/423.1 |
| 4,494,531 | 1/1985 | Gianturco | 128/1 |
| 4,619,246 | 10/1986 | Molgaard-Nielsen et al. | 128/1 |
| 4,643,184 | 2/1987 | Mobin-Uddin | 128/303 |
| 4,650,466 | 3/1987 | Luther | 604/95 |
| 4,662,885 | 5/1987 | DiPisa, Jr. | 623/12 |
| 4,675,361 | 6/1987 | Ward, Jr. | 525/92 |
| 4,688,553 | 8/1987 | Metals | 128/1 |
| 4,727,873 | 3/1988 | Mobin-Uddin | 128/303 |
| 4,781,177 | 11/1988 | Lebigot | 128/897 |
| 4,793,348 | 12/1988 | Palmaz | 128/325 |
| 4,817,600 | 4/1989 | Herms et al. | 128/303 |
| 4,832,055 | 5/1989 | Palestrant | 128/899 |
| 4,873,978 | 10/1989 | Ginsburg | 128/345 |
| 4,925,698 | 5/1990 | Klausner et al. | 427/2 |
| 4,943,460 | 7/1990 | Markle et al. | 428/36.9 |
| 4,957,501 | 9/1990 | Lahille et al. | 606/200 |
| 4,959,074 | 9/1990 | Halpern et al. | 623/66 |
| 4,969,891 | 11/1990 | Gewertz | 606/200 |
| 4,980,231 | 12/1990 | Baker et al. | 428/36.9 |
| 4,990,156 | 2/1991 | Lefebvre | 606/200 |
| 4,998,539 | 3/1991 | Delsanti | 128/898 |
| 5,002,582 | 3/1991 | Guire et al. | 623/66 |
| 5,026,607 | 6/1991 | Kiezulas | 428/423.7 |
| 5,035,706 | 7/1991 | Giantureo et al. | 606/198 |
| 5,037,656 | 8/1991 | Pitt et al. | 424/443 |
| 5,037,677 | 8/1991 | Halpern et al. | 427/338 |
| 5,059,205 | 10/1991 | El-Nounou et al. | 606/200 |
| 5,071,407 | 12/1991 | Termin et al. | 604/104 |
| 5,102,402 | 4/1992 | Dror et al. | 604/265 |
| 5,108,418 | 4/1992 | Lefebvre | 606/200 |
| 5,108,419 | 4/1992 | Reger et al. | 606/200 |
| 5,133,733 | 7/1992 | Rasmussen et al. | 606/200 |
| 5,147,379 | 9/1992 | Sabbaghian et al. | 606/206 |
| 5,152,777 | 10/1992 | Goldberg et al. | 606/200 |
| 5,160,342 | 11/1992 | Reger et al. | 606/200 |
| 5,160,790 | 11/1992 | Elton | 428/412 |
| 5,234,458 | 8/1993 | Metais | 606/200 |
| 5,242,462 | 9/1993 | El-Nounou et al. | 606/200 |
| 5,250,613 | 10/1993 | Bergstrom et al. | 525/54.1 |
| 5,304,121 | 4/1994 | Sahatjian | 604/53 |
| 5,324,304 | 6/1994 | Rasmussen | 606/200 |
| 5,330,768 | 7/1994 | Park et al. | 424/501 |
| 5,370,657 * | 12/1994 | Irie | 606/200 |
| 5,380,299 | 1/1995 | Fearnot et al. | 604/265 |
| 5,383,928 | 1/1995 | Scott et al. | 623/1 |
| 5,419,760 | 5/1995 | Narciso, Jr. | 604/8 |
| 5,443,458 | 8/1995 | Eury | 604/891.1 |
| 5,447,724 | 9/1995 | Helmus et al. | 424/426 |
| 5,449,382 | 9/1995 | Dayton | 623/1 |
| 5,451,428 * | 9/1995 | Rupp | 427/2.12 |
| 5,464,650 | 11/1995 | Berg et al. | 427/2.3 |
| 5,512,055 | 4/1996 | Domb et al. | 604/265 |
| 5,545,208 | 8/1996 | Wolff et al. | 623/1 |
| 5,562,922 | 10/1996 | Lambert | 424/486 |
| 5,578,075 | 11/1996 | Dayton | 623/1 |
| 5,591,227 | 1/1997 | Dinh et al. | 623/1 |
| 5,601,595 | 2/1997 | Smith | 606/200 |
| 5,605,696 | 2/1997 | Eury et al. | 424/423 |
| 5,616,608 | 4/1997 | Kinsella et al. | 514/449 |
| 5,624,411 | 4/1997 | Tuch | 604/265 |
| 5,626,605 | 5/1997 | Irie et al. | 606/200 |
| 5,626,862 | 5/1997 | Brem et al. | 424/426 |
| 5,669,933 | 9/1997 | Simon et al. | 600/200 |
| 5,674,192 | 10/1997 | Sahatjian et al. | 604/28 |
| 5,679,400 | 10/1997 | Tuch | 427/2.14 |
| 5,702,754 | 12/1997 | Zhong | 427/2.12 |
| 5,716,981 | 2/1998 | Hunter et al. | 514/449 |
| 5,722,984 | 3/1998 | Fischell et al. | 606/198 |
| 5,733,925 | 3/1998 | Kunz et al. | 514/449 |
| 5,776,184 | 7/1998 | Tuch | 623/1 |
| 5,837,008 | 11/1998 | Berg et al. | 623/1 |
| 5,837,313 * | 11/1998 | Ding et al. | 427/2.21 |
| 6,156,373 * | 12/2000 | Zhong | 427/2.28 |

OTHER PUBLICATIONS

M.D. Darcy, T.P. Smith, D.W. Hunter et al., "Short–Term Prophylaxis of Pulmonary Embolism by Using a Retrievable Vena Cava Filter," pp. 836–838, 1986, *AJR*, 147.

G.S. Dorfman, M.D., "Percutaneous Inferior Vena Caval Filters," pp. 987–991, 1990 *Radiology*, 174.

A.M. Fadali, S.R. Topaz, M.M. Ameli, V.I. Gott, "A Filtering Device for the Prevention of Particulate Embolization During the Course of Cardiac Surgery," pp. 634–639, 1968, *Surgery*, 64.

P.J. Golueke, W.V. Garrett, J.E., Thompson et al., "Interruption of the Vena Cava by Means of the Greenfield Filter: Expanding the Indications," pp. 111–117. 1988, *Surgery*, 103.

C.J. Grassi, "Inferior Vena Caval Filters: Analysis of Five Currently Available Devices," pp. 813–821, Apr. 1991, *AJR*, 156.

R.W. Gunther et al., "Vena Caval Filter to Prevent Pulmonary Embolism: Experimental Study," pp. 315–320, Aug., 1985, *Radiology*, 156.

T. Irie, S. Furui, T. Yamauchi, K. Makita, S. Sawada, E. Takenaka, "Relocatable Gianturco Expandable Metallic Stents," pp. 575–577, 1991, *Radiology*, 178.

D. Kim, D.H. Porter, J.B. Siegel & M. Simon, "Perforation of the Inferior Vena Cava with Aortic and Vertebral Penetration by a Suprarenal Greenfield Filter," pp. 721–723, 1989, *Radiology*, 172.

G. Lund, J. Rysavy, E. Salomonowitz et al., "A New Vena Caval Filter for Percutaneous Placement and Retrieval: Experimental Study," pp. 369–372, 1984, *Radiology*, 152.

G. Lund, J. Rysavy, D.W. Hunter, W.R. Castaneda–Zuniga, L. Amplatz, "Retrievable Vena Caval Filter Percutaneously Introduced", pp. 831, 1985 *Radiology*, 155.

Maass, D. et al., "The Helix Filter: A New Vena Caval Filter for the Prevention of Pulmonary Embolism", *J. Cardiovasc, Surg.*, 1985, 2 pgs.

A.M. Palestrant, M. Prince, M. Simon, "Comparative In Vitro Evaluation of the Nitinol Inferior Vena Cava Filter," 16 pages, 1982, *Radiology*, 145.

M. Simon, A.M. Palestrant, "Transvenous Devices for the Management of Pulmonary Embolism," pp. 308–318, 1980, *Cardio Vascular and Interventional Radiology*, 3.

M.J. Wallace, K. Ogawa, K. Wright, C.H. Carrasco, W. Richi, C. Charnasgavej, "Inferior Vena Caval Stent Filter," pp. 1247–1250, 1986, *AJR*, 147.

* cited by examiner

THROMBOSIS FILTER HAVING A SURFACE TREATMENT

FIELD OF THE INVENTION

The present invention generally pertains to intravascular devices. In particular, the present invention pertains to intravascular thrombosis filters.

BACKGROUND OF THE INVENTION

Pulmonary embolism is a recognized medical emergency, and is often caused by venous thrombosis. Physiological conditions such as venous intima damage, blood flow retention, and coagulation abnormalities are often the cause of venous thrombosis. Recognized treatments for venous thrombosis include anti-coagulant medication therapy, thrombolytic therapy, thrombectomy, and inferior vena cava thrombosis filtering or blocking procedures.

When an inferior vena cava thrombosis filtering or blocking procedure is selected, it can be performed using either a laparotomy procedure, or by percutaneously inserting a thrombosis filter. A laparotomy procedure is a surgical procedure performed under general anesthesia. Because it is necessary to discontinue anti-coagulant therapy prior to surgery, this procedure, itself, is susceptible to thrombosis formation.

The second option is to intravenously insert a thrombosis filter into the vascular system. In particular, the thrombosis filter is mounted into the inferior vena cava in order to prevent large emboli from passing to the lungs. Since this procedure requires only a local anesthetic, percutaneous filter insertion is recognized as an effecateous procedure. Thrombosis filters, however, become encapsulated to the vein wall through neointimal hyperplasia. Neointimal hyperplasia is the subsequent increase in endothelial cell production caused by the irritation of the lining membrane of the blood vessel. Neointima grows from the inner wall of the blood vessel, around the thrombosis filter and its anchors. This process can occur within two or three weeks after implantation, rendering many thrombosis filters unremovable by a single percutaneous process without significant vessel trauma.

SUMMARY OF THE INVENTION

The present invention comprises a thrombosis filter having various surface treatments. In each preferred embodiment of the thrombosis filter of the present invention, the filter includes a body element, a plurality of struts, and a surface treatment.

The body element serves as the support structure to which the plurality of struts are attached. Generally, the struts are attached to the body element and extend longitudinally and radially therefrom forming a generally conical structure. The struts, themselves, are shaped and spaced apart in a manner which allows them to prevent emboli from passing into the lungs via the circulatory system when in use in a vessel lumen. Each individual strut has both a joining end and a free end. The joining end of the strut is secured to the body element. The free end of the strut, however, extends away from the body element and bears against the inner wall of the blood vessel. Vessel-engaging tips of various designs may be placed on the free end of a strut in order to facilitate the strut's engagement with the blood vessel wall. The combination of the body element with its plurality of struts radiating therefrom brace the thrombosis filter against the inner wall of the blood vessel within the blood vessel lumen.

A surface treatment is applied to at least a portion of the thrombosis filter in order to regulate neointimal growth around the thrombosis filter and its anchor elements. Inhibiting the neointimal growth allows for the removal of the thrombosis filter with reduced retrieval forces and limited damage to the vessel wall. The surface treatment in preferred embodiments constitutes, in part, an anti-proliferative or an anti-angiogenesis drug.

In one embodiment, the drug is an anti-angiogenesis agent. Anti-angiogenesis agents are substances which have the ability to impede the local proliferation of blood vessels, thereby blocking the necessary "food supply" of the growing endothelial cell mass. This anti-angiogenesis drug may be coated directly upon portions of the thrombosis filter, itself, through a dipping or spraying process, or the drug may be incorporated into a polymeric material as a carrier which regulates the rate of drug release to the vessel wall.

In a further embodiment, the thrombosis filter contains a first and a second surface treatment layer. The first surface treatment layer, coated upon at least a portion of the thrombosis filter, possesses endothelial cell growth enhancing properties. The second surface treatment layer, coated upon at least a portion of the first surface layer, includes an anti-proliferative or an anti-angiogenesis drug. In this arrangement, the second surface treatment layer is dissolvable or generally biodegradable. Thus, when the filter is first placed in the vessel lumen, the anti-proliferative or anti-angiogenesis drug inhibits neointimal growth as discussed above. However, if the thrombosis filter remains engaged with the vessel wall for an extended period, the second layer will dissolve exposing the first layer. The first layer then promotes endothelial cell growth causing the eventual permanent encapsulation of the anchor elements of the filter within the blood vessel wall.

The surface treatment may be applied directly to a portion of the filter or the surface treatment may be applied to a substrate which, in turn, is applied to a portion of the filter. Preferably, the substrate is disposed about the free ends of the struts and may take the form of a pad, a tubular structure, or a band.

The present invention is thus an improved thrombosis filter. Additional features of the invention and the advantages derived therefrom, and the various scopes and aspects of the invention will become apparent from the drawings, the description of the preferred embodiments of the invention, and the claims.

DETAILED DESCRIPTION OF THE DRAWINGS

The following detailed description should be read with reference to the drawings in which similar elements in different drawings are numbered the same. The drawings, which are not necessarily to scale, depict selected preferred embodiments and are not intended to limit the scope or spirit of the invention.

Figure 1:
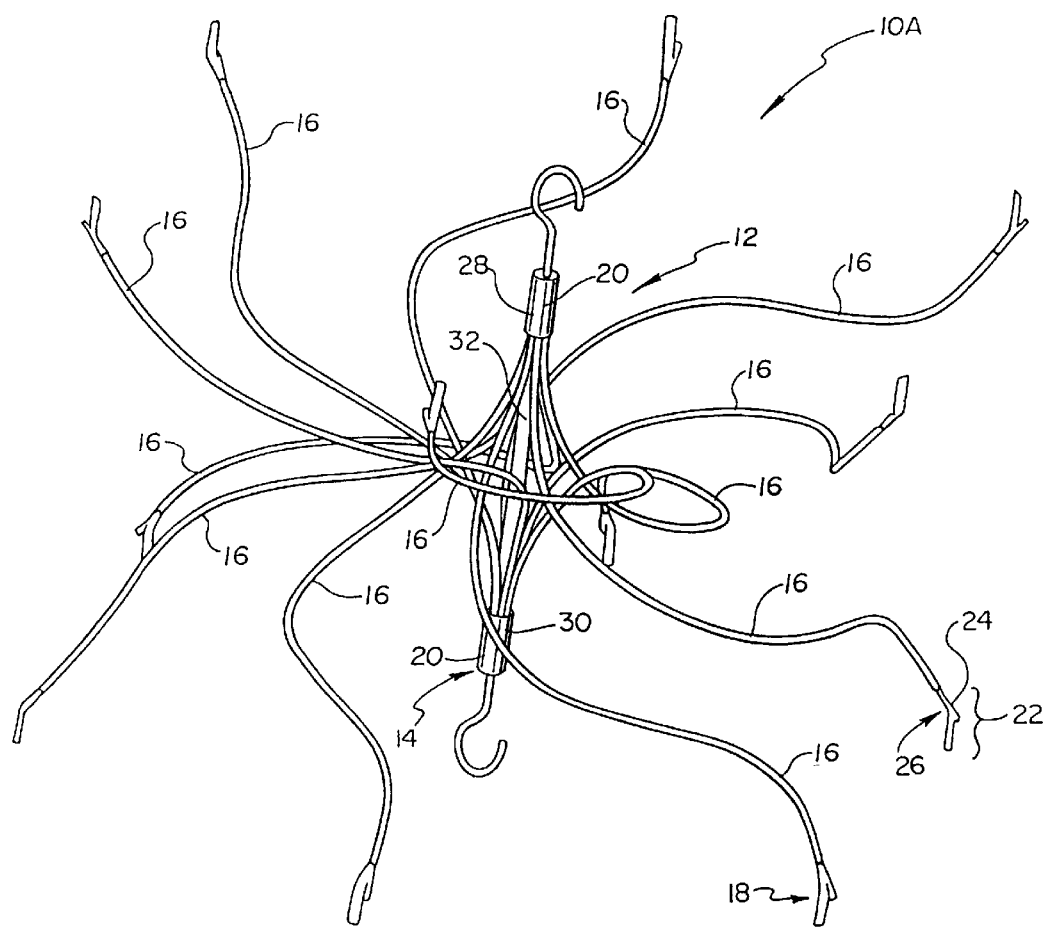
FIG. 1 is a perspective view of a thrombosis filter in accordance with an exemplary embodiment of the present invention.
Figure 3:
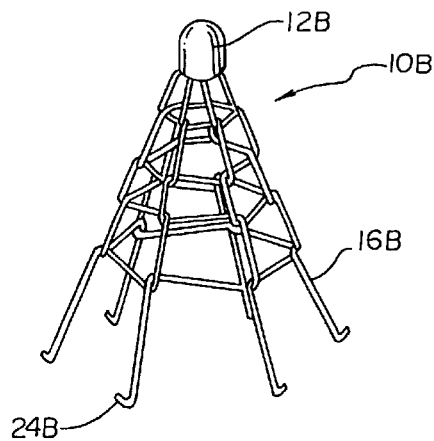
FIG. 3 is a perspective view of an alternative thrombosis filter in accordance with the present invention.
Figure 8:
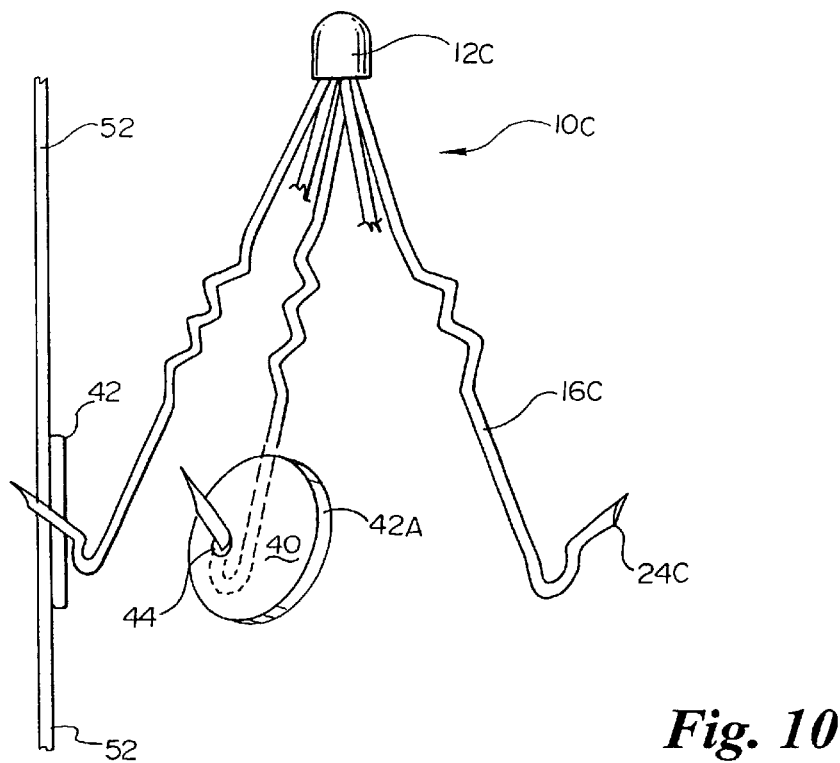
FIG. 8 is a perspective view of another alternative thrombosis filter having an alternative surface treatment in the form of a pad.

The present invention may be incorporated into a wide variety of thrombosis filters including the types illustrated in FIGS. 1, 3, and 8. The structure, function, and use of such thrombosis filters are generally described in U.S. Pat. No. 5,601,595, which is assigned to the assignee of the present invention, and is hereby incorporated by reference.

Refer now to FIG. 1, which illustrates a perspective view of a thrombosis filter 10A in accordance with the present invention. Thrombosis filter 10A includes first and second body elements 12 and 14, respectively. Each body element 12 and 14 includes a plurality of struts 16. Each strut includes a free end 18 and a joining end 20. Free end 18 terminates in a vessel-engaging tip portion 22, which may be attached to the strut free end 18 or formed therein. The vessel-engaging tip portion 22 preferably includes a sharpened portion 24 and an adjacent flexible pad portion 26. The joining ends 20 of struts 16 on both first and second body elements 12 and 14 are joined at hubs 28 and 30, respectively.

Figure 2:
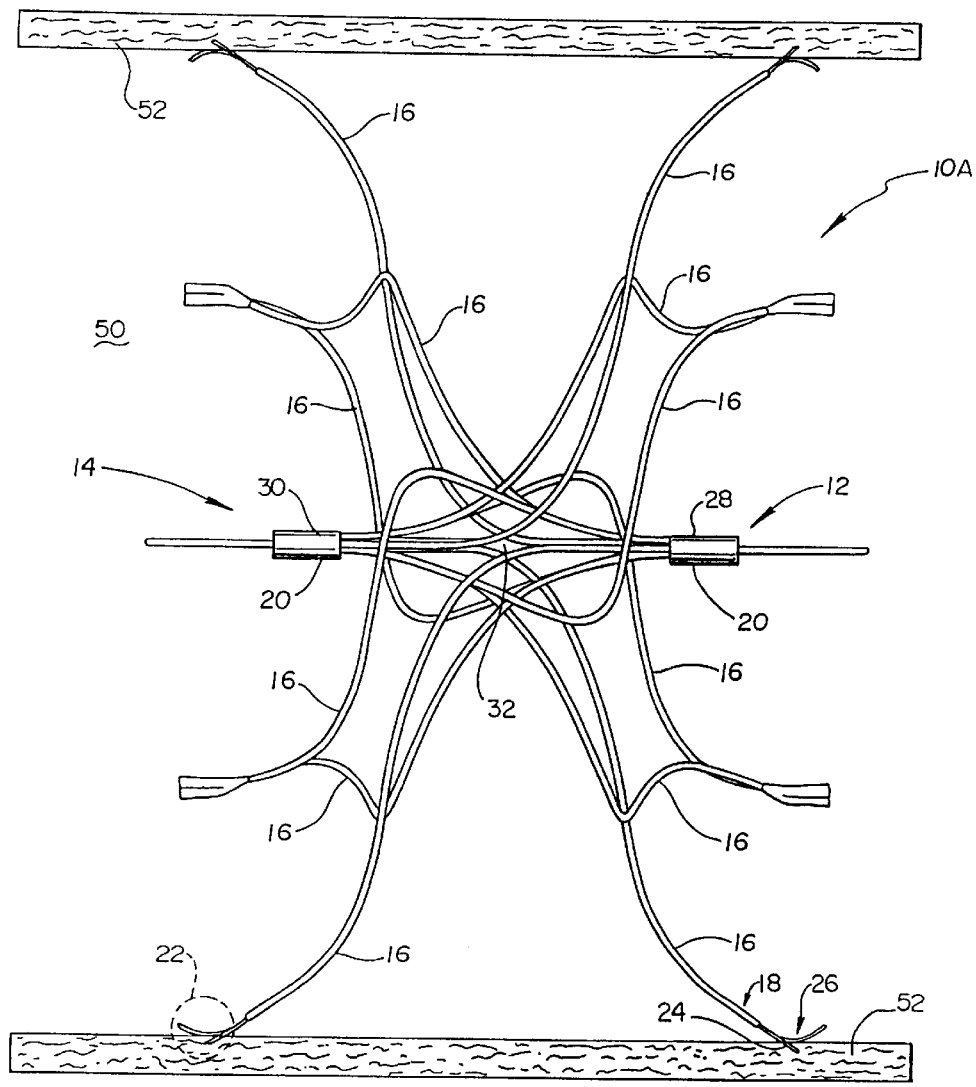
FIG. 2 is a plan view of the thrombosis filter of FIG. 1 positioned in a vascular lumen.

FIG. 2 shows a side view of a thrombosis filter 10A deployed within a vessel lumen 50. Specifically, FIG. 2 illustrates how the vessel-engaging tips 22 contact the vessel wall 52. As depicted, sharpened portions 24 of vessel-engaging tips 22 engage the wall 52 of vessel lumen 50. Further engagement of sharpened portion 24 is resisted by the adjacent flexible pad portion 26 abutting the vessel wall 52.

FIG. 3 is a perspective view of an alternative thrombosis filter 10B in accordance with the present invention. Similar to the filter 10A in FIG. 1, thrombosis filter 10B is designed to capture emboli circulating in the vascular system. The three basic units of thrombosis filter 10B are the body element 12B, the struts 16B, and vessel-engaging tips 24B. Unlike the filter 10A in FIG. 1, struts 16B of filter 10B intertwine as they radiate outwardly from the body element 12B, forming hooks as vessel-engaging tips 24B.

FIG. 8 is a perspective view of another alternative thrombosis filter 10C in accordance with the present invention. The three basic units of thrombosis filter 10C are body portion 12C, struts 16C and vessel-engaging tips 24C. Unlike the struts 16B of filter 10B illustrated in FIG. 3, the struts 16C of filter 10C are not intertwined.

The design variations between the thrombosis filter 10A of FIG. 1, the thrombosis filter 10B of FIG. 3, and the thrombosis filter 10C of FIG. 8 depict just a few of the modifications possible in optimizing the filtering process. Regardless of the modification, however, the basic units of one or more body portions, struts, and tips remain present. For purposes of clarity and illustration only, the nomenclature of filter 10A is used with reference to FIGS. 4–7 and the nomenclature of filter 10C is used with reference to FIGS. 8–10. However, each surface treatment described herein may be implemented on virtually any thrombosis filter including filters 10A, 10B, and 10C.

Figure 4:
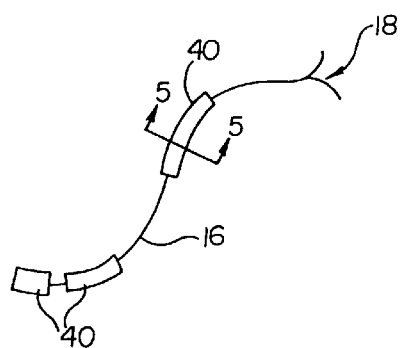
FIG. 4 is a side view of a wire strut selectively having a surface treatment.

FIG. 4 is a side view of a wire strut selectively having a surface treatment 40. Strut 16 is comprised of a bio-compatible material, preferably having shape memory or super elastic properties. Possible filter materials include Nitinol, stainless steel, tungsten, platinum, tantalum, chromium alloy, and silicone, among others. The shape of strut 16 varies upon use and preference. Variations in the struts 16 shape include round, ribbon, helical, serpentine, and straight, among others.

Figure 5:
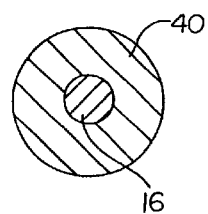
FIG. 5 is a cross-sectional view taken at line 5—5 in FIG. 4.

FIG. 5 is a cross-sectional view taken at line 5–5 in FIG. 4. This view illustrates the surface treatment coating 40 on strut 16. Along strut 16, the surface treatment 40 may cover the entire strut 16 or be present on selected portions. The surface treatment 40 may be present on the joining end 20, the free end 18, or the vessel-engaging tip 22 of strut 16, or any combination thereof. Surface treatment 40 may be present as a thin surface coating, or a visible layer.

In one embodiment, surface treatment 40 is comprised, in part, of an anti-proliferative or anti-angiogenic drug. Additional components may be added to the anti-proliferative or anti-angiogenic drug in order to alter the function of the surface treatment 40. To prevent the aggregation of platelets, fibrin, clotting factors, and cellular elements of the blood as a result of the implementation of the thrombosis filter 10A, the anti-proliferative or anti-angiogenic drug may also contain non-thrombogenic properties, or an additional anti-thrombogenic drug can be incorporated with the other drugs. Additionally, anti-angiogenesis agents such as taxol may be included in the surface treatment 40 to impede endothelial cell growth around the thrombosis filter's 10A structure. Alternatively, phospholipid-based biomaterials, such as phophorylcholine may be used in the surface treatment 40. These additional components may be added singularly or in combination to the anti-proliferative or anti-angiogenic drug comprising the surface treatment 40.

In a further embodiment, surface treatment 40 is a dissolvable or biodegradable layer. The rate at which the surface treatment 40 dissolves is regulated by the structure and composition of the surface treatment 40, itself. The structure of surface treatment 40 is either amorphous, crystalline, or a combination of the two. The ability of surface treatment 40 to dissolve is proportional to amorphous and crystalline properties the surface treatment 40 possesses. By modifying the ratio of the two properties, the ability of surface treatment 40 to dissolve either increases or decreases. This process works likewise between hydrophobic and hydrophilic compositional material.

In order to control the release or dissolving rate, the anti-proliferative or anti-angiogenic drug may be incorporated into a bio-compatible or biodegradable polymeric material forming surface treatment 40. Polyethylene oxide (PEO), polypropylene oxide (PPO), polylactic acid (PLA), polyglycolic acid, and polycaprolactone, among others, are examples of such polymeric material. Either the homopolymer or the copolymer forms of these materials may be utilized in the incorporation with the anti-proliferative or anti-angiogenic drug. When this surface treatment 40 is added to the structure of the thrombosis filter 10A, additional structural properties are also transferred. These properties include selective rigidity and superior wall engaging performance, among others.

In some embodiments, the anti-proliferative or anti-angiogenic drug, or drug in combination with a polymeric material, can be sprayed or dip-coated onto the filter structure. Single or multiple coats may be applied, preferably in a solvent carrier which is evaporated to form the coated structure. When a polymeric material is used, the antiproliferative or anti-angiogenic drug can be admixed with the polymer prior to application. Other therapeutic agents can also be admixed if desired.

Figure 6:
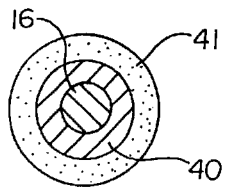
FIG. 6 is an alternative cross-sectional view taken at line 5—5 in FIG. 4.

FIG. 6 is an alternative cross-sectional view taken at line 5—5 in FIG. 4 of an alternative embodiment of the present invention. In this embodiment, the thrombosis filter 10A contains multiple (preferably two) surface treatment layers. The first surface treatment layer 40, coated upon portions of the thrombosis filter 10A, specifically strut 16, possesses endothelial cell growth enhancing properties. The second surface treatment layer 41, coated upon the first surface layer 40, includes an anti-proliferative or anti-angiogenic drug. In this arrangement, the second surface treatment layer 41 is dissolvable or biodegradable. If the thrombosis filter 10A remains engaged within the vessel lumen 50 (from FIG. 2) for an extended period, the second layer 41 will dissolve or be absorbed, exposing the first layer 40. The first layer 40 then promotes endothelial cell growth causing the eventual permanent encapsulation of the filter 10A within the blood vessel lumen 50. Endothelial cell growth enhancing materials can be included alone or in combination with a polymeric carrier, such as the substrate 42 described with reference to FIGS. 8–10.

Figure 7:
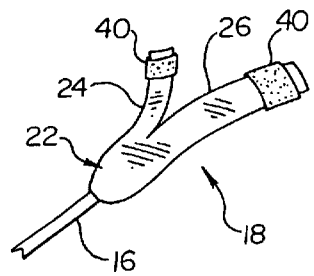
FIG. 7 is a partial perspective view of a vessel-engaging tip selectively coated with a surface treatment.

FIG. 7 is a partial perspective view of a preferred vessel-engaging tip portion 22 coupled with a surface treatment 40. Vessel-engaging tip portion 22 extends from or is attached to free end 18 of strut 16. The vessel-engaging tip portion 22 includes a sharpened portion 24 and an adjacent flexible pad portion 26. Surface treatment 40 may be applied to selective areas of the vessel-engaging tip portion 22. Areas of particular interest are the entire sharpened portion 24 and the portion of the adjacent flexible pad 26 which contacts the vessel wall. However, surface treatment 40 need not be limited to these described areas.

Figure 9:
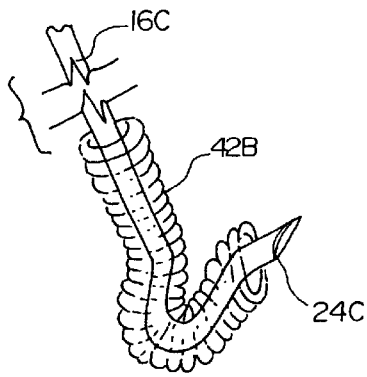
FIG. 9 is a perspective view of a vessel-engaging tip having an alternative surface treatment in the form of a tube.
Figure 10:
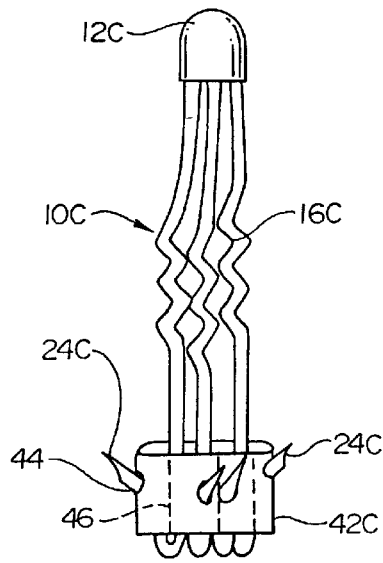
FIG. 10 is a is a perspective view of a thrombosis filter having an alternative surface treatment in the form of a band.

Refer now to FIGS. 8–10, which illustrate perspective views of alternative embodiments of the present invention as applied to filter 10C. As previously described, the three basic units of thrombosis filter 10C are body portion 12C, struts 16C, and vessel-engaging tips 24C. However, the various embodiments of FIGS. 8–10 generally relate to the surface treatment 40 and thus may be incorporated into any thrombosis filter, including filters 10A, 10B, and 10C.

Specifically, FIGS. 8–10 illustrate alternative embodiments of the surface treatment 40 wherein the surface treatment 40 is applied to a substrate 42, which in turn is applied to the filter 10C. FIG. 8 illustrates the substrate 42 in the form of a pad 42A, FIG. 9 illustrates the substrate 42 in the form of a tubular structure 42B, and FIG. 10 illustrates the substrate 42 in the form of a band 42C. Those skilled in the art will recognize that the form of the substrates 42A, 42B, and 42C described herein are merely exemplary and many forms may be employed without departing from the scope or spirit of the invention. For purposes of discussion, substrates 42A, 42B, and 42C may be generically referred to as substrate 42.

Referring to FIG. 8, the substrate 42 is shown in the form of a pad 42A which is secured to the strut 16C. Preferably, the surface treatment 40 is applied to the surface that comes into contact with the vessel wall 52. The pad 42A may incorporate a hole 44 sized to accommodate the tip 24C of the strut 16C for attachment thereto.

Referring now to FIG. 9, the substrate 42 is shown in the form of a tubular structure 42B which is secured to the strut 16C. Preferably, the surface treatment 40 is applied to the exterior surface of the tube 42B such that the surface treatment 40 comes into contact with the vessel wall 52. The tubular structure 42B includes a lumen sized to accommodate the tip 24C of the strut 16C such that the tube may be slid onto the tip 24C of the strut 16C, much like a sock.

Referring finally to FIG. 10, the substrate 42 is shown in the form of a band 42C which is secured about the struts 16C when the filter 10C is in a collapsed state (as shown). The band 42C may include a plurality of holes 44 sized to accommodate the tips 24C of the struts 16C such that the band 42C may be loaded thereon. In addition, the band 42C may include a plurality of separation lines 46, preferably disposed between the holes 44. The separation lines 46 may be lines of weakness in the band 42C such as serrated lines. When the filter expands, the band 42C separates along the separation lines 46 to essentially form a plurality of pads as discussed with reference to FIG. 8. As with the other embodiments, the surface treatment 40 is preferably applied to the exterior surface of the band 42C such that the surface treatment 40 comes into contact with the vessel wall 52.

Substrate 42 may be formed of a wide variety of suitable materials including the materials which form the struts 16 of the filter 10A and other polymer carriers. Thus, the surface treatment 40 may be sprayed, dipped, or otherwise coated onto the substrate 42 as described previously. Alternatively, the surface treatment 40 may be admixed or otherwise incorporated into the material of the substrate 42 such that the material of the substrate 42 functions as a carrier of the surface treatment material 40.

Numerous characteristics and advantages of the invention covered by this document have been set forth in the foregoing description. It will be understood, however, that this disclosure is, in many aspects, only illustrative. Changes may be made in details, particularly in matters of shape, size, and arrangement of parts without exceeding the scope of the invention. The invention's scope is defined, of course, in the language in which the appended claims are expressed.

What is claimed is:

1. A thrombosis filter element for placement within a blood vessel lumen defined by a vessel wall comprising:
   a body element from which a plurality of struts radiate, the plurality of struts each having a joining end, wherein the joining end of the plurality of struts attach to the body element, the plurality of struts each having a free end, wherein each of the free ends of the plurality of struts contact the blood vessel wall; and
   a surface treatment covering at least a portion of the thrombosis filter, wherein the surface treatment comprises two layers, a first surface treatment layer located between a second surface treatment layer and the portion of the thrombosis filter, the first surface treatment layer having properties which enhance endothelial cell growth, and the second surface treatment layer including an anti-proliferative or anti-angiogenic drug.

2. A thrombosis filter element according to claim 1, wherein the drug is taxol.

3. A thrombosis filter element according to claim 1, wherein the drug is non-thrombogenic.

4. A thrombosis filter element according to claim 1, wherein the second surface treatment layer is dissolvable, wherein the dissolving rate may be varied depending upon the structure and composition of the second surface treatment layer.

5. A thrombosis filter element according to claim 1, wherein the surface treatments incorporate, respectively, the anti-proliferative or anti-angiogenic drug and the endothelial cell growth enhancer with a bio-compatible polymeric material, or a combination of the surface treatment layers with or without the incorporation of the bio-compatible polymeric material.

6. A thrombosis filter element according to claim 1, wherein the first and second surface treatment layers cover the plurality of free ends of the struts in contact with the vessel wall.

7. A thrombosis filter element according to claim 1, wherein the surface treatments, or some combination of the first surface treatment layer and the second surface treatment layer, are coated upon at least a portion of the thrombosis filter element through a dipping or spraying process.

8. A thrombosis filter element for placement within a blood vessel lumen comprising:

a body element, wherein the body element is aligned parallel with a longitudinal axis of the blood vessel lumen, wherein from the body element a plurality of struts radiate, the plurality of struts comprised of a bio-compatible material selected from the group consisting of nitinol, stainless steel, tantalum, gold, silicone, and combinations thereof, wherein the plurality of struts extend outward from the body element, including joining ends of the plurality of struts attached to the body element, and free ends, wherein a portion of the free ends of the plurality of struts engage the blood vessel wall; and an anti-proliferative or anti-angiogenic drug constituting a surface treatment covering at least a portion of the thrombosis filter element, wherein the surface treatment may cover the entire or only discrete regions of the thrombosis filter element, wherein the surface treatment incorporates the anti-proliferative or anti-angiogenic drug with a biocompatible polymeric material, wherein the bio-compatible polymeric material is biodegradable.

9. A thrombosis filter element according to claim 8, wherein the addition of the surface treatment alters the overall structural properties of the thrombosis filter element, wherein the surface treatment adds rigidity thereby enhancing performance of the thrombosis filter element.

10. A thrombosis filter element for placement within a blood vessel lumen comprising:

a body element, wherein the body element is aligned parallel with a longitudinal axis of the blood vessel lumen, wherein from the body element a plurality of struts radiate, the plurality of struts comprised of a bio-compatible material selected from the group consisting of nitinol, stainless steel, tantalum, gold, silicone, and combinations thereof, wherein the plurality of struts extend outward from the body element, including joining ends of the plurality of struts attached to the body element, and free ends, wherein a portion of the free ends of the plurality of struts engage the blood vessel wall; and an anti-proliferative or anti-angiogenic drug constituting a surface treatment covering at least a portion of the thrombosis filter element, wherein the surface treatment may cover the entire or only discrete regions of the thrombosis filter element, wherein the surface treatment is applied to a substrate which covers the portion of the thrombosis filter.

11. A thrombosis filter according to claim 10, wherein the substrate is disposed about the free ends of the struts.

12. A thrombosis filter according to claim 11, wherein the substrate comprises a plurality of pads.

13. A thrombosis filter according to claim 12, wherein the pads each include a hole, and wherein the struts are disposed in the holes of the pads.

14. A thrombosis filter according to claim 11, wherein the substrate comprises a plurality of tubes.

15. A thrombosis filter according to claim 14, wherein the tubes each include a lumen, and wherein the struts are disposed in the lumens of the tubes.

16. A thrombosis filter according to claim 11, wherein the substrate comprises a band surrounding the struts when the filter is in a collapsed configuration.

17. A thrombosis filter according to claim 16, wherein the band separates into a plurality of segments when the filter is in an expanded configuration.

* * * * *